(12) United States Patent
Paquet, Jr.

(10) Patent No.: US 8,361,555 B2
(45) Date of Patent: Jan. 29, 2013

(54) HYDROXY ALKYL ISOCYANURATES

(75) Inventor: Donald Albert Paquet, Jr., Troy, MI (US)

(73) Assignee: E I du Pont de Nemours and Company, Wilmington, DE (US)

( * ) Notice: Subject to any disclaimer, the term of this patent is extended or adjusted under 35 U.S.C. 154(b) by 249 days.

(21) Appl. No.: 12/747,077

(22) PCT Filed: Dec. 22, 2008

(86) PCT No.: PCT/US2008/087917
§ 371 (c)(1),
(2), (4) Date: Jun. 9, 2010

(87) PCT Pub. No.: WO2009/086253
PCT Pub. Date: Jul. 9, 2009

(65) Prior Publication Data
US 2010/0272907 A1  Oct. 28, 2010

Related U.S. Application Data

(60) Provisional application No. 61/009,288, filed on Dec. 27, 2007.

(51) Int. Cl.
*B05D 3/02* (2006.01)
*C08G 73/10* (2006.01)
*C08G 18/08* (2006.01)
(52) U.S. Cl. .............. 427/385.5; 524/600; 524/589; 528/322

(58) Field of Classification Search .............. 524/101, 524/589, 600; 528/322; 427/385.5
See application file for complete search history.

(56) References Cited

U.S. PATENT DOCUMENTS

| 3,088,948 A | 5/1963 | Little et al. |
| 4,031,040 A | 6/1977 | denOtter et al. |
| 4,063,020 A | 12/1977 | denOtter et al. |
| 4,198,505 A | 4/1980 | Frisch et al. |
| 4,235,977 A | 11/1980 | Frisch et al. |
| 4,245,080 A | 1/1981 | Frisch et al. |
| 4,514,526 A | 4/1985 | Marx et al. |
| 5,116,945 A * | 5/1992 | Osawa et al. .............. 530/215 |
| 6,130,297 A | 10/2000 | Ramesh |

FOREIGN PATENT DOCUMENTS

| EP | 622387 A | 11/1994 |
| EP | 661351 A | 7/1995 |
| WO | 03/040111 A | 5/2003 |

OTHER PUBLICATIONS

Andreas Kaplan: "Polyester/beta-hydroxyalkylamide Powder Coatings"; European Coatings Journal; vol. 6; 1998; pp. 448-453.*

* cited by examiner

*Primary Examiner* — John J. Figueroa
*Assistant Examiner* — Atnaf Admasu
(74) *Attorney, Agent, or Firm* — Brian J Myers

(57) ABSTRACT

This invention relates to hydroxy alkyl isocyanurates, coating compositions comprising hydroxy alkyl isocyanurates and methods for producing hydroxy alkyl isocyanurates. Dried and cured coating compositions containing the hydroxy alkyl isocyanurates provide excellent durability, gloss and distinctness of image.

16 Claims, No Drawings

HYDROXY ALKYL ISOCYANURATES

FIELD OF THE INVENTION

This invention relates to hydroxy alkyl isocyanurates, coating compositions comprising hydroxy alkyl isocyanurates and to methods for forming the hydroxy functional isocyanurates. The coatings and methods described herein are especially suitable for use in the automotive original manufacturer (OEM) industries or automotive refinish industries.

DESCRIPTION OF THE RELATED ART

The isocyanurate group provides coatings with a high level of durability, as it is a very stable chemical moiety that is not easily degraded by everyday environmental conditions. The isocyanurate group is most often incorporated into a coating composition via the isocyanurate trimer of a polyisocyanate. The use of isocyanurate trimers is generally found in coating composition used in the refinish industry through the use of isocyanurate trimers of polyisocyanates.

There have been numerous attempts to incorporate the isocyanurate functionality into coating compositions without using isocyanate functional isocyanurates. U.S. Pat. No. 4,063,020 to Stamicarbon, discloses a mixed hydroxymethyl-hydroxyalkyl isocyanurate. The mixed isocyanurate comprises at least one nitrogen of the isocyanurate ring capped with a hydroxymethyl group and at least one of the remaining nitrogens of the isocyanurate group capped with a hydroxyalkyl group. The goal of this invention is to produce hydroxy functional isocyanurate compounds wherein the hydroxy groups have differing reactivity ratios.

U.S. Pat. No. 4,514,526 to BASF produces a storage-stable polyol dispersion comprising tris-hydroxyalkyl isocyanurates, at least one other polyol and optionally a dispersion stabilizer. The tris-hydroxyalkyl isocyanurates of this disclosure have up to four carbons in the alkyl group.

U.S. Pat. No. 3,088,948 to Allied Chemical discloses tris-2-hydroxyalkyl isocyanurates that are soluble only in highly polar solvents such as dialkyl formamides.

U.S. Pat. No. 6,130,297 to Cytec discloses the use of tris-(2-carboxyethyl)isocyanurate as one component in a crosslinking composition suitable for producing epoxy powder coating resins.

The above isocyanurate derivatives generally have a low solubility in all but very polar solvents, making them difficult to use in a liquid coating composition.

The present invention produces an isocyanurate derivative that is soluble in the solvent systems typically used for coating composition formulations and provides hydroxy functionality that is reactive with a variety of commonly used crosslinking agents.

SUMMARY OF THE INVENTION

The present invention relates to a method of producing a coating on a substrate; said method comprising the steps of; (i) applying a layer of a coating composition onto the surface of a substrate; and (ii) curing said layer of coating composition, wherein said coating composition comprises a hydroxy functional isocyanurate of the structure

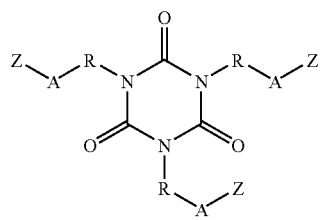

wherein each R is independently selected from hydroxy functional alkyl having from 3 to 20 carbons;

A is independently selected from O, NH, NR1, or a direct bond; and

Z is independently selected from the group consisting of hydrogen, —C(O)R1, —C(O)NHR1, —C(O)OR1, —C(O)NR1R1, and an alkyl group having in the range of from 1 to 30 carbons that may be substituted with O, N, P, or Si; and wherein each R1 is independently selected from the group consisting of an alkyl group having in the range of from 1 to 30 carbons that may optionally be substituted with O, N, P, or Si; and optionally substituted aryl group having in the range of from 6 to 20 carbons that may optionally be substituted with O, N, P, or Si.

The present disclosure also relates to a method of producing a coating on a substrate; said method comprising the steps of; (i) applying a layer of a coating composition onto the surface of a substrate; and (ii) curing said layer of coating composition, wherein said coating composition comprises a hydroxy functional isocyanurate of the structure

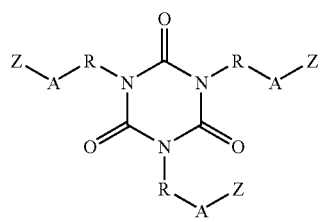

wherein each R is independently selected from hydroxy functional alkyl having from 3 to 20 carbons;

A is independently selected from O, NH, NR1, or a direct bond; and

Z is independently selected from the group consisting of hydrogen, —C(O)R1, —C(O)NHR1, —C(O)OR1, —C(O)NR1R1, and an alkyl group having in the range of from 1 to 30 carbons that may be substituted with O, N, P, or Si; and wherein each R1 is independently selected from the group consisting of an alkyl group having in the range of from 1 to 30 carbons that may optionally be substituted with O, N, P, or Si; and optionally substituted aryl group having in the range of from 6 to 20 carbons that may optionally be substituted with O, N, P, or Si.

The present disclosure also relates to a hydroxy functional isocyanurate of the formula;

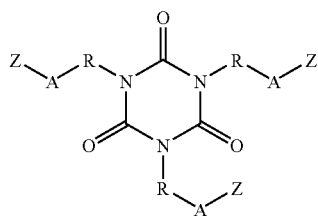

wherein each

R is independently selected from hydroxy functional alkyl having from 3 to 20 carbons;

A is independently selected from O, NH, NR1, or a direct bond; and

Z is independently selected from the group consisting of hydrogen, —C(O)R1, —C(O)NHR1, —C(O)OR1, —C(O)NR1R1, and an alkyl group having in the range of from 1 to 30 carbons that may be substituted with O, N, P, or Si; and wherein each R1 is independently selected from the group consisting of an alkyl group having in the range of from 1 to 30 carbons that may optionally be substituted with O, N, P, or Si; and optionally substituted aryl group having in the range of from 6 to 20 carbons that may optionally be substituted with O, N, P, or Si.

DETAILED DESCRIPTION OF THE INVENTION

The features and advantages of the present invention will be more readily understood, by those of ordinary skill in the art, from reading the following detailed description. It is to be appreciated that certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. Also, the disclosure of these ranges is intended as a continuous range including every value between the minimum and maximum values.

As used herein, "one-pack" and "one component" coating compositions are used interchangeably and mean a coating composition having both the crosslinkable and crosslinking components stored together in one container optionally containing solvent and/or other adjuvants. The one-pack coating composition is typically applied to a substrate and then dried and cured at elevated temperatures to form a coating on the substrate surface having desired coating properties, such as, high gloss, mar-resistance and resistance to environmental etching.

As used herein, "two-pack" and "two component" coating compositions are used interchangeably and mean a coating composition having the crosslinkable and crosslinking components stored in separate containers. Typically, one container contains a crosslinkable component and optionally contains solvent and/or other adjuvants; the other container contains the crosslinking component and optionally solvent and/or other adjuvants. The individual containers are typically sealed to increase the shelf life of the components of the coating composition. The components are mixed just prior to use to form a pot mix, which has a limited pot life, typically in the range from a few minutes (15 minutes to 45 minutes) to a few hours (4 hours to 8 hours). The pot mix is applied as a layer of a desired thickness on a substrate. After application, the layer dries and cures at ambient or elevated temperatures to form a coating on the substrate surface having desired coating properties, such as, high gloss, mar-resistance and resistance to environmental etching.

The term "crosslinkable component" refers to the compounds and/or the polymers that react with the crosslinking component to form the film forming binder of the coating composition.

The term "crosslinking component" refers to the compounds and/or polymers that react with the crosslinkable components to form the film forming binder of the coating composition.

The term "film forming binder" or "binder" means the components that react to form a crosslinked network. Pigments, catalysts, solvents, or any other additives that do not become a permanent part of the network are typically not included in this definition.

The inventive hydroxy functional isocyanurates have a structure according to;

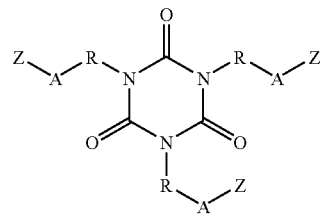

wherein each

R is independently selected from hydroxy functional alkyl having from 3 to 20 carbons;

A is independently selected from O, NH, NR1, or a direct bond; and

Z is independently selected from the group consisting of hydrogen, —C(O)R1, —C(O)NHR1, —C(O)OR1, —C(O)NR1R1, and an alkyl group having in the range of from 1 to 30 carbons that may be substituted with O, N, P, or Si; and wherein each R1 is independently selected from the group consisting of an alkyl group having in the range of from 1 to 30 carbons that may optionally be substituted with O, N, P, or Si; and optionally substituted aryl group having in the range of from 6 to 20 carbons that may optionally be substituted with O, N, P, or Si. Preferably, R is —$CH_2CH(OH)CH_2$—.

The desired hydroxy functional isocyanurates can be produced using one of two general methods. According to general method (I), cyanuric acid can be contacted with an epoxy functional molecule to produce the desired product. In the general method (II), an epoxy functional isocyanurate can be contacted with a molecule that has functional group that is reactive with an epoxy group.

Preferably, in both of the general methods, the reaction stoichiometry is chosen so that the final product is a tris-hydroxy functional isocyanurate molecule. However, it should be understood that the actual product may be a mixture containing mono-, di-, and tri-substituted products. For clarity, the product will be discussed in terms of the tri-substituted products.

In the general method (I), cyanuric acid is reacted with an epoxy functional molecule as illustrated by the following general reaction scheme;

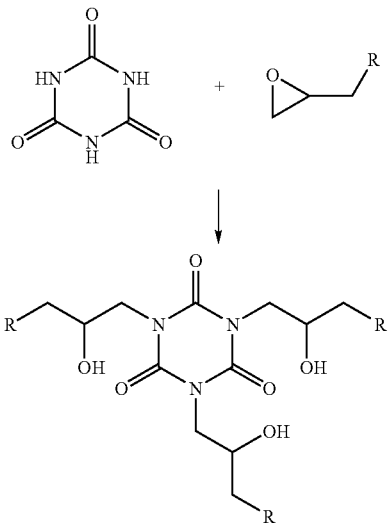

In the above general reaction scheme, R can be a linear or branched aliphatic containing 1 or more carbon atoms or a cycloaliphatic molecule containing in the range of from 3 or more carbon atoms. The upper range of carbon atoms is not particularly limited. However, for purposes of this invention, the upper range will assumed to be about 30 carbon atoms. R can optionally be substituted with hydroxy, ester, ether, amide, silane, siloxane, ketone, urea and/or urethane groups.

Suitable epoxy functional molecules can be chosen from;
1. Aliphatic epoxides. Preferably, the epoxide group is a terminal epoxide group. The epoxide can contain in the range of from 5 or more carbon atoms. Preferably, the epoxide contains in the range of from 6 to 25 carbon atoms and most preferably, the epoxide contains in the range of from 7 to 20 carbon atoms. Optionally, the aliphatic portion may be substituted with hydroxy, silane, siloxane and/or amine.
2. Epoxy functional ethers. Epoxy ethers may be simple alkyl ethers or they may be polyethers. For simple alkyl ethers, it is preferred to use alkyl glycidyl ethers wherein the alkyl ether portion contains in the range of from 1 to 30 carbon atoms. More preferably the alkyl ether portion contains in the range of from 4 to 25 carbon atoms and, most preferably the alkyl ether portion contains in the range of from 6 to 20 carbon atoms. In the case of polyethers, it is preferred to use a polyalkylene glycol ether of the formula A-$(OR^2)_n$—$OR^3$, wherein A is an epoxy containing group, preferably a glycidyl group; $R^2$ is an alkyl group selected from the group consisting of —$CH_2CH_2$—, —$CH_2CH(CH_3)$—, —$(CH_2)_3$—, —$(CH_2)_4$— and a combination thereof; and $R^3$ is H or an alkyl group containing from 1 to 6 carbon atoms and n is in the range of from 2 to 500. Preferably the polyethers are terminated with an epoxy group.
3. Epoxy esters. Preferred epoxy esters are glycidyl esters of aliphatic carboxylic acids. The aliphatic carboxylic acids generally have in the range of from 2 to 30 carbon atoms. More preferably, the aliphatic carboxylic acids have in the range of from 4 to 25 carbon atoms and most preferably, have in the range of from 6 to 20 carbon atoms. The aliphatic carboxylic acids may optionally be substituted. One useful epoxy ester is CARDURA E10®, which is the glycidyl ester of neodecanoic acid, available from Hexion Specialty Chemicals, Houston, Tex.
4. Epoxy ketones. The epoxy functional ketone preferably has the epoxy group on the terminal end of the molecule. Preferably the epoxy functional ketone contains in the range of from 5 to 30 carbon atoms. More preferably, the epoxy functional ketone contains in the range of from 6 to 25 carbon atoms, and more preferably, it contains in the range of from 7 to 20 carbon atoms.
5. Epoxy alcohols. Epoxy functional alcohols can also be used with cyanuric acid to the desired product. The simplest epoxy alcohol is glycidol or 2,3-epoxy-1-propanol. Preferably, the epoxy alcohols contain in the range of from 3 to 30 carbon atoms. More preferably, epoxy alcohols contain in the range of from 4 to 25 carbon atoms and most preferably, contain in the range of from 5 to 20 carbon atoms.
6. Epoxy urethanes. Epoxy urethanes contain both an epoxy functionality and a urethane group. Preferably, the epoxy group is terminal on the molecule. One simple example is an epoxy urethane that is the reaction product of 2,3-epoxy-1-propanol and 1-hexane isocyanate. It is preferred that the epoxy urethane contain in the range of from 4 to 30 carbon atoms. More preferably, the epoxy urethane contains in the range of from 5 to 25 carbon atoms and more preferably, contains from 6 to 20 carbon atoms.

General Method (II)

In the second method, an epoxy functional isocyanurate can be contacted with a functional group that is reactive with an epoxide. Suitable functional groups include, for example, alcohol, amine, carboxylic acid, amide and/or an anhydride to produce the desired product. Preferably, the epoxy functional isocyanurate is tris-glycidyl isocyanurate (TGIC) although any suitable epoxy functional isocyanurate could be used. TGIC has the formula;

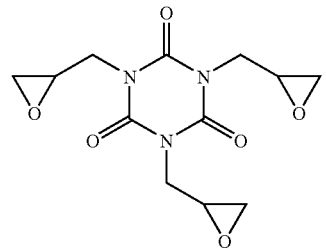 [SMILES: O=c1n(CC2CO2)c(=O)n(CC2CO2)c(=O)n1CC1CO1]

TGIC or an epoxy functional isocyanurate molecule can be reacted with a variety of epoxy reactive molecules to form the desired hydroxy functional isocyanurate molecules. Epoxy reactive molecules are well known in the art. The following list is a sample of the preferred examples of each.
1. Alcohols. Alcohols react with epoxy groups to form hydroxy functional ethers. Suitable alcohols are aliphatic alcohols preferably containing from 1 to 30 carbon atoms. More preferably, the alcohols contain in the range of from 4 to 25 carbons and most preferably, the alcohols contain in the range of from 6 to 20 carbon atoms.

2. Amides. Amides react with epoxy groups to form hydroxy functional amides. Suitable amides contain at least one nitrogen-hydrogen bond that is capable of reacting with the epoxy group. Preferred amides have in the range of from 2 to 30 carbon atoms. More preferably, the amides have in the range of from 4 to 25 carbon atoms and, most preferably they have in the range of from 6 to 20 carbon atoms.

3. Carboxylic acids. Carboxylic acids can react with epoxy groups to form hydroxy functional esters. Preferred carboxylic acids are acids having in the range of from 2 to 30 carbon atoms. More preferably, the carboxylic acids have in the range of from 4 to 25 carbon atoms and, most preferably they have in the range of from 6 to 20 carbon atoms. Examples of suitable carboxylic acids include, for example, acetic acid, propionic acid, butyric acid, pentanoic acid, hexanoic acid, cyclohexane carboxylic acid, pivalic acid, stearic acid, neodecanoic acid, isononanoic acid (3,5,5-trimethylhexanoic acid), 4. Carboxylic anhydrides. Carboxylic anhydrides react with epoxy groups to form a molecule having a hydroxy functionality, an ester group and a free carboxylic acid. Depending upon the stoichiometry and the reaction conditions used when reacting the epoxy group with the anhydride, multiple products can be formed. After the anhydride reacts, the free carboxylic acid can react with another TGIC epoxy group or the free carboxylic acid can react with a hydroxyl group to form another ester group. The hydroxy group can be on the same molecule or it could be a hydroxyl group from another TGIC/anhydride molecule. Preferred carboxylic anhydrides have in the range of from 4 to 30 carbons. More preferably, they have in the range of from 6 to 25 carbon atoms, and more preferably they have in the range of from 8 to 20 carbon atoms. More preferred are carboxylic anhydrides that are half esters. Molecules such as these have one free carboxylic acid functional group and one ester group.

5. Amines. Suitable amines are aliphatic primary and aliphatic secondary amines. Care should be taken to carefully control the stoichiometry when employing primary amines as these amines can react with two equivalents of epoxide forming dimers or even polymers depending upon the conditions employed. Preferred are secondary amines containing in the range of from 2 to 30 carbon atoms. More preferably, the amines contain in the range of from 4 to 25 carbon atoms and more preferably, they contain in the range of from 6 to 20 carbon atoms.

The inventive tris-hydroxyalkyl isocyanurate (THIC) compounds are preferably used in coating compositions and more preferably, in automotive coating compositions. Such compositions can be used as primers, basecoats, and/or clearcoats.

The THIC compounds of the present invention are preferably used as the crosslinkable component of a coating composition. As these compounds are tri-substituted, they have the potential to form highly crosslinked films. The inventive THIC can be present in a coating composition in the range of from 100 percent by weight to 1 percent by weight of the crosslinkable component.

Other crosslinkable components that may be used with THIC of the present invention are known to those of ordinary skill in the art and include, for example, polyacrylates, polyesters, polyethers, polyurethanes, polyureas, or a combination thereof. Preferably, these polymers also contain functional groups that are able to react with the crosslinking components to form a crosslinked network. Suitable functional groups include hydroxy, amino, epoxy, silane, siloxane, carboxy, urethane, urea, or a combination thereof. Preferably, the other crosslinkable components are polyacrylates, polyesters, polyethers or a combination thereof and the functional groups are hydroxy, amino, silane, siloxane or a combination thereof.

The coating composition of the present invention includes a crosslinking component. The crosslinking component can be chosen from polyisocyanates, melamines, blocked polyisocyanates and a combination thereof.

Melamine formaldehyde condensates are generally preferred for a one-pack coating composition. In general, these are aldehyde condensation products of melamine, urea, benzoguanamine, or a similar compound. Usually, the aldehyde employed is formaldehyde, although useful products can be made from other aldehydes, such as acetaldehyde, crotonaldehyde, acrolein, benzaldehyde, furfural, and others.

Of the melamines, monomeric or polymeric melamines that are partially or fully alkylated are generally preferred. These melamines are organic solvent-soluble and are commercially available, for example, under the tradename CYMEL® from Cytec Industries, Inc., West Patterson, N.J. Preferred crosslinking agents are methylated, butylated and/or isobutylated melamine formaldehyde resin having a degree of polymerization of about 1 to 3. One preferred melamine, for a good balance of properties, is a fully butylated resin known as CYMEL 1156®.

Other possible crosslinking agents can also be used, such as urea formaldehyde, benzoguanamine formaldehyde and blocked or unblocked polyisocyanates or compatible mixtures of any of the forgoing crosslinkers.

For instance, the melamine crosslinking agents described above can be substituted for or optionally combined with any of the conventional blocked polyisocyanate crosslinking agents for enhanced film properties. Typical blocking agents are alcohols, ketimines, oximes, pyrazoles or a combination thereof.

Polyisocyanates are typically used for two-component coating compositions. Useful polyisocyanates are aliphatic polyisocyanates, cycloaliphatic polyisocyanates, aromatic polyisocyanates, and polyisocyanate adducts thereof. Polyisocyanate adducts can contain isocyanurate, allophanate, uretidione and/or biuret groups.

Examples of suitable aliphatic, cycloaliphatic and aromatic polyisocyanates that can be used include the following: 2,4-toluene diisocyanate, 2,6-toluene diisocyanate ("TDI"), 4,4-diphenylmethane diisocyanate ("MDI"), 4,4'-dicyclohexyl methane diisocyanate, ("$H_{12}$MDI"), 3,3'-dimethyl-4,4'-biphenyl diisocyanate ("TODI"), 1,4-benzene diisocyanate, trans-cyclohexane-1,4-diisocyanate, 1,5-naphthalene diisocyanate ("NDI"), 1,6-hexamethylene diisocyanate ("HDI"), 4,6-xylene diisocyanate, isophorone diisocyanate, ("IPDI"), other aliphatic or cycloaliphatic di-, tri- or tetra-isocyanates, such as, 1,2-propylene diisocyanate, tetramethylene diisocyanate, 2,3-butylene diisocyanate, octamethylene diisocyanate, 2,2,4-trimethyl hexamethylene diisocyanate, dodecamethylene diisocyanate, omega-dipropyl ether diisocyanate, 1,3-cyclopentane diisocyanate, 1,2-cyclohexane diisocyanate, 1,4-cyclohexane diisocyanate, 4-methyl-1,3-diisocyanatocyclohexane, dicyclohexyl-methane-4,4'-diisocyanate, 3,3'-dimethyl-dicyclohexyl-methane 4,4'-diisocyanate; polyisocyanates having isocyanurate structural units; isocyanates having uretidione structural units; adducts of 3 molecules of diisocyanates and 1 molecule of water; allophanates, trimers and biurets of hexamethylene diisocyanate, allophanates, trimers and biurets of isophorone diisocyanate and the isocyanurate of hexane diisocyanate.

MDI, HDI, TDI and isophorone diisocyanate are preferred because of their commercial availability.

Tri-functional isocyanates also can be used, such as, triphenyl methane triisocyanate, 1,3,5-benzene triisocyanate, 2,4,6-toluene triisocyanate. Trimers of diisocyanates, such as, the trimer of hexamethylene diisocyanate, sold as TOLONATE® H DT from Rhodia Corporation and the trimer of isophorone diisocyanate are also suitable.

An isocyanate functional adduct can be used, such as, for example, the adduct of a polyisocyanate and a polyol or the adduct of a polyisocyanate and a polyamine. Any of the aforementioned polyisocyanates can be used with a polyol and/or polyamine to form an adduct. Preferably, polyols, such as, trimethylol alkanes, particularly, trimethylol propane or ethane can be used to form an adduct.

Coatings compositions containing the THIC compounds according to the present invention can also include other additives. Additives such as solvents, curing catalysts, UV light absorbers, light stabilizers, pigments, dyes, fillers, rheology control agents, viscosity modifiers, are typically added depending upon the final use of the coating composition and are well known to those of ordinary skill in the art.

The coating composition of the present invention can be a solventborne coating composition. Some of the suitable solvents include aromatic hydrocarbons, such as petroleum naphtha or xylenes; esters, such as, ethyl acetate, butyl acetate, t-butyl acetate, isobutyl acetate or hexyl acetate; and glycol ether esters, such as propylene glycol monomethyl ether acetate. The amount of organic solvent added depends upon the desired solids level as well as the desired amount of VOC of the composition. If desired, the organic solvent may be added to both the crosslinking and crosslinkable components of the coating composition.

The amount of solvent added to the coating composition may be adjusted to provide the composition with a VOC (volatile organic content) in the range of from 0.12 kilograms (1.0 pounds per gallon) to 0.78 kilograms (6.5 pounds per gallon) of the solvent per liter of the coating composition.

The coating composition preferably includes one or more catalysts to enhance crosslinking of the components during curing. Generally, the coating composition includes in the range of from 0.005 percent to 2 percent, preferably in the range of from 0.01 to 1 percent and more preferably in the range of from 0.02 percent to 0.7 percent of the catalyst, the percentages being in weight percentages based on the total weight of the crosslinkable and crosslinking component solids. These catalysts are preferably added to the binder component. Typical catalysts include dibutyl tin dilaurate, dibutyl tin diacetate, dibutyl tin dichloride, dibutyl tin dibromide, triphenyl boron, tetraisopropyl titanate, triethanolamine titanate chelate, dibutyl tin dioxide, dibutyl tin dioctoate, tin octoate, zinc octoate, zinc naphthenate, aluminum titanate, aluminum chelates, zirconium chelate, amine salts of sulfonic acids, hydrocarbon phosphonium halides, such as, ethyl triphenyl phosphonium iodide and other such phosphonium salts, and other catalysts or mixtures thereof known to those skilled in the art.

To improve weatherability of the coating, 0.1 to 5 weight percent, preferably 0.5 to 2.5 weight percent and more preferably 1 to 2 weight percent of ultraviolet light stabilizers screeners, quenchers and antioxidants can be added to the composition, the percentages being based on the total weight of the binder and crosslinking components solids. Typical ultraviolet light screeners and stabilizers include for example, benzophenones, such as hydroxy dodecycloxy benzophenone, 2,4-dihydroxy benzophenone, and hydroxy benzophenones containing sulfonic acid groups; benzoates, such as dibenzoate of diphenylol propane and tertiary butyl benzoate of diphenylol propane; triazines, such as 3,5-dialkyl-4-hydroxyphenyl derivatives of triazine and sulfur containing derivatives of dialkyl-4-hydroxy phenyl triazine, hydroxy phenyl-1,3,5-triazine; triazoles, such as 2-phenyl-4-(2,2'-dihydroxy benzoyl)-triazole and substituted benzotriazoles, such as hydroxy-phenyltriazole; hindered amines, such as bis(1,2,2,6,6 entamethyl-4-piperidinyl sebacate) and di[4(2,2,6,6, tetramethyl piperidinyl)]sebacate; and any mixtures of any of the above.

Typical pigments that can be used in the coating composition are filler pigments such as talc, china clay, barytes, carbonates, silicates, and color pigment such as metallic oxides such as titanium dioxide, zinc oxide and iron oxide and carbon black and organic colored pigments and dyes. Also useful as pigments that can be added to the composition include the following: metallic oxides, such as titanium dioxide, zinc oxide, iron oxides of various colors, carbon black; filler pigments, such as talc, china clay, barytes, carbonates, silicates; and a wide variety of organic colored pigments, such as quinacridones, copper phthalocyanines, perylenes, azo pigments, indanthrone blues, carbazoles, such as carbozole violet, isoindolinones, isoindolones, thioindigo reds, benzimidazolinones; metallic flake pigments, such as aluminum flakes, mica flakes, pearlescent flakes, or a combination thereof.

Typically useful conventional additives include rheology control agents, for example, RESIFLOW® S (polybutylacrylate), BYK® 320 or 325 (silicone leveling agents, supplied by BYK Chemie, Wallingford, Conn.), BYK® 347 (polyether-modified siloxane, supplied by BYK Chemie, Wallingford, Conn.) and rheology control agents, such as, fumed silica. The inclusion of additional additives will depend on the intended use of the coating composition. For example, any additives that would adversely affect the clarity of the cured coating will not be included if the composition is used as a clear coating.

The coating composition can be formulated as a one-pack coating composition or as a two-pack coating composition. Application of the coating composition is typically by a spray process, for example, electrostatic spraying or pneumatic spraying. However, the coating composition can be applied by flow coating, roller coating or using a dip process.

The coating composition can be formulated as a primer composition, a color containing basecoat formulation or a clear coating composition. As used herein, the term "clear" refers to the appearance of the dried and cured layer of film. Prior to curing, the composition may be clear or it may be translucent or even opaque.

Once a layer of the coating composition is applied to a substrate, the solvent can optionally be removed (known as flash-dried or flashed) by allowing to stand for several minutes at ambient or elevated temperatures, with or without airflow directed at the substrate to facilitate solvent removal. The layer of coating composition can be cured at ambient temperature or it may be cured at elevated temperatures.

In a typical automotive painting procedure, a layer of primer composition is applied to a suitably prepared substrate and the applied layer is cured. A layer or layers of basecoat composition is then applied to the primed substrate and the basecoat layer(s) are optionally flashed for several minutes to remove at least a portion of the solvent. A layer or layers of clearcoat composition are then applied to the dried but uncured basecoat. The applied layers of basecoat/clearcoat compositions can optionally be flashed and then, based upon the crosslinking components, can be cured at ambient or elevated temperatures to form a durable cured coating composition.

Suitable substrates for applying the coating composition of the present invention include automobile bodies, any and all items manufactured and painted by automobile sub-suppliers, frame rails, commercial trucks and truck bodies, including but not limited to beverage bodies, utility bodies, ready mix concrete delivery vehicle bodies, waste hauling vehicle bodies, and fire and emergency vehicle bodies, as well as any potential attachments or components to such truck bodies, buses, farm and construction equipment, truck caps and covers, commercial trailers, consumer trailers, recreational vehicles, including but not limited to, motor homes, campers, conversion vans, vans, pleasure vehicles, pleasure craft snow mobiles, all terrain vehicles, personal watercraft, motorcycles, boats, and aircraft. The substrate further includes industrial and commercial new construction and maintenance thereof; cement and wood floors; leather; walls of commercial and residential structures, such office buildings and homes; amusement park equipment; concrete surfaces, such as parking lots and drive ways; asphalt and concrete road surface, wood substrates, marine surfaces; outdoor structures, such as bridges, towers; coil coating; railroad cars; printed circuit boards; machinery; OEM tools; signage; fiberglass structures; sporting goods; and sporting equipment.

EXAMPLES

The information provided regarding the source of availability of materials used herein is accurate as of the time of this disclosure. Unless otherwise specified, all chemicals are available from the Aldrich Chemical Company, Milwaukee, Wis.

CARDURA® E10 is available from Hexion Specialty Chemicals, Houston, Tex.

AROMATIC® 100 solvent is available from ExxonMobil, Houston, Tex.

ROCRYL® 430 is 2-hydroxypropyl methacrylate and is available from Rohm and Haas, Philadelphia, Pa.

Gamma-methacryloylpropyl trimethoxysilane is available from GE Silicones, Fairfield, Conn. as SILQUEST® Y-11396NT.

VAZO® 67 initiator is available from DuPont, Wilmington, Del.

FASCAT® 2003 stannous octoate is available from Arkema, Inc., Philadelphia, Pa.

DESMODUR® H polyisocyanate is available from Bayer Material Science, Pittsburgh, Pa.

DISPARLON®-955 surfactant and K-CAT® XC2227 catalyst are available from King Industries, Norwalk, Conn.

CYMEL® 303 melamine is available from Cytec Industries, Stamford, Conn.

TINUVIN® 292 and TINUVIN® 384 are available from Ciba Specialty Chemicals, Tarrytown, N.Y.

TOLONATE HDT® is the isocyanurate trimer of hexamethylene diisocyanate and is available from Rhodia, Inc., Cranbury, N.J.

Test Procedures

Ford Viscosity was measured according to ASTM D1200 using a #4 Ford cup.

Gloss was measured at 20° using a Byk-Gardener Glossmeter.

Distinctness of Image (DOI) was measured using a Hunterlab Model RS 232 (HunterLab, Reston, Va.).

Acid Etch testing was completed by placing 5 drops of 0.2N sulfuric acid onto coated panels and heating the panels to 60° C. for 12 hours. The depth of etching was then measured.

Dry Mar Resistance procedure. Panels were coated with a thin layer of Bon Ami abrasive supplied by Faultless Starch/Bon Ami Corporation, Kansas City, Mo. The panels were then tested for mar damage for 10 double rubs against a green felt wrapped fingertip of A.A.T.C.C. Crockmeter (Model CM-1, Atlas Electric Devices Corporation, Chicago, Ill.). The dry mar resistance was recorded as percentage of gloss retention by measuring the 20° gloss of the marred areas versus non-marred areas of the coated panels.

Wet Mar Resistance procedure. Similar Procedure to that used in Dry Mar Resistance above was used to test wet mar resistance, except the abrasive medium used was wet alumina slurry instead of Bon Ami abrasive. The composition of the wet alumina slurry was as follows:

| Ingredient | Amount (grams) |
|---|---|
| Deionized water | 294 |
| ASE-60 ® Thickener[1] | 21 |
| AMP-95% (10% solution in DI water)[2] | 25 |
| Aluminum oxide (120# grit)[3] | 7 |

[1]Associate thickener supplied by Rohm and Haas Company, Philadelphia, Pennsylvania.
[2]Supplied by Aldrich Chemicals, Milwaukee, Wisconsin.
[3]Abrasive Supplied by MDC Industries, Philadelphia, Pennsylvania.

Preparation of Tris-Hydroxyalkyl Isocyanurates

Example 1

In a round neck flask equipped with a stirrer, Dean Stark trap, condenser, nitrogen inlet, and a thermometer was added a mixture of 10 parts of cyanuric acid and 58 parts of CARDURA® E10 in 32 parts ethylene glycol. The mixture was stirred for 12 hours at 150° C. The reactor was then cooled to 130° C. and 30 parts xylene was added. Ethylene glycol was removed by azeotropic distillation over a period of 16 hours. The final product was a clear solution at 70% non volatile in xylene.

Preparation of Acrylic Polymer 1 RCS37919

| Ingredient | Amount (parts by weight) |
|---|---|
| Portion 1 | |
| AROMATIC ® 100 | 71.619 |
| n-butanol | 55.24 |
| Portion 2 | |
| styrene | 59.128 |
| isobutyl methacrylate | 70.928 |
| ROCRYL ® 430 | 59.128 |
| butyl acrylate | 17.738 |
| gamma-methacyloylpropyl trimethoxysilane | 384.206 |
| Portion 3 | |
| AROMATIC ® 100 | 84.776 |
| VAZO ® 67 | 47.047 |
| Portion 4 | |
| AROMATIC ® 100 | 5.65 |

The ingredients of portion 1 were added to a mixing vessel equipped with a thermometer, addition funnels, stirrer, nitrogen inlet, and a heating mantle. The mixture was heated to reflux (248° C. to 257° C.). Portion 2 was mixed thoroughly and added to an addition funnel. Portion 3 was mixed thoroughly and added to a second addition funnel. Portion 2 was added to the reaction mixture over a 300 minute period. Portion 3 was added concurrently with Portion 2 over a 330 minute period. When the addition of portion 3 was complete, portion 4 was added to the reaction mixture. The reaction was held at reflux for an additional 60 minutes, then cooled to 158° C. and filtered. The mixture was then allowed to cool to room temperature and used as is.

Preparation of Polyester 1 RCP30418

| Ingredient | Amount (parts by weight) |
|---|---|
| Portion 1 | |
| epsilon-caprolactone | 172 |
| FASCAT ® 2003 | 5.1 |
| AROMATIC ® 100 | 23.3 |
| Portion 2 | |
| dimethylol propionic acid | 258 |
| pentaerythritol | 41.8 |
| Portion 3 | |
| epsilon-caprolactone | 344 |
| Portion 4 | |
| AROMATIC ® 100 | 18.1 |
| Portion 5 | |
| ethyl 3-ethoxypropionate | 97.4 |

The ingredients of portion 1 were charged, in order, to a reactor equipped with a thermometer, addition funnel, stirrer, nitrogen inlet, distillation head and a heating mantle. The mixture was heated to 69° C. to 71° C. The ingredients of portion 2 were then mixed and added to the reaction mixture while maintaining a temperature of 69° C. to 71° C. When the addition was complete, the reaction was heated to 170° C. to 200° C. to distill water from the reaction until an acid number less than 3.5 was attained. The reaction was then cooled to 129° C. to 131° C. Portion 3 was then added over a 30 minute period at such a rate so that the exotherm did not exceed 140° C. The reaction was held at 129° C. to 131° C. until the Gardner-Holdt viscosity of a 150 gram resin sample diluted with 17.5 grams ethyl 3-ethoxypropionate was Z to Z2. When the correct viscosity was achieved, portion 5 was added to the reaction mixture. The reaction was then cooled to room temperature and portion 6 was added. The mixture was used as is.

Preparation of SCA in Polyester VM-7991

| Ingredient | Amount (parts by weight) |
|---|---|
| Portion 1 | |
| Polyester 1 | 55.084 |
| 2-ethyl-1,3-hexanediol | 21.337 |
| 2-ethyl hexanol | 10.712 |
| Portion 2 | |
| benzyl amine | 3.315 |
| butyl acetate | 5.209 |
| Portion 3 | |
| DESMODUR ® H | 2.607 |
| butyl acetate | 1.736 |

The ingredients of portion 1 were charged to a reactor equipped with a thermometer, addition funnel, stirrer and nitrogen inlet. The ingredients of portion 2 were then added and stirred for 1½ minutes. Portion 3 was added as quickly as possible while maintaining the temperature at room temperature or alternately cooling the mixture. After stirring for 5 minutes, the mixture was used as is.

Coating Examples

The ingredients below were mixed in the order shown in a suitable mixing vessel. All units given below are in parts by weight. Each of the coating compositions were then activated with 45 parts by weight of TOLONATE HDT® polyisocyanate.

| Ingredient | Coating 1 | Coating 2 | Coating 3 (comparative) |
|---|---|---|---|
| Example 1 | 10.5 | 21 | 0 |
| CYMEL ® 303 | 31 | 31 | 31 |
| Acrylic Polymer 1 | 4.76 | 4.76 | 4.76 |
| Trimethyl orthoacetate | 4.5 | 4.5 | 4.5 |
| TINUVIN ® 292 | 1 | 1 | 1 |
| TINUVIN ® 384 | 2.11 | 2.11 | 2.11 |
| SCA in Polyester | 21.85 | 21.85 | 21.85 |
| 2-ethyl-1,3-hexanediol | 1.32 | 1.32 | 1.32 |
| Polyester 1 | 5.59 | 5.59 | 5.59 |
| DISPARLON ®-955 | 1 | 1 | 1 |
| K-CAT ® XC2227 | 0.24 | 0.24 | 0.24 |
| Dodecyl benzene sulfonic acid | 2.85 | 2.85 | 2.85 |

Panels were prepared by electrocoating and priming steel panels. The primed steel panels were coated with a layer of a black waterborne basecoat composition (available from DuPont as 686-). The waterborne basecoat was flashed for 5 minutes at 82° C. Each of the activated coating composition were applied to the flashed steel panels to a film build of 38 to 51 micrometers (1.5 to 2 mils). The coated panels were flashed in a horizontal position for 10 minutes at room temperature then baked for 30 minutes at 140° C. The coated panels were then tested.

| TEST | Coating 1 | Coating 2 | Coating 3 (comparative) |
|---|---|---|---|
| #4 Ford viscosity (seconds) | 47.5 | 48 | 48 |
| Acid Etch depth | 0.68 | 0.5 | 1.1 |
| 20° Gloss | 90 | 89 | 88 |
| DOI | 82 | 86 | 84 |
| Wet Mar (% gloss retention) | 92 | 96 | 89 |
| Dry Mar (% gloss retention) | 91 | 93 | 87 |

The testing shows that coating compositions 1 and 2 containing the inventive hydroxy functional isocyanurate, posses superior acid etch resistance, and generally improved 20° gloss, DOI and gloss retention after both wet and dry mar abrasion tests when compared to coating composition 3 containing none of the inventive hydroxy functional isocyanurates.

What is claimed is:

1. A coating composition comprising a hydroxy functional isocyanurate of the formula;

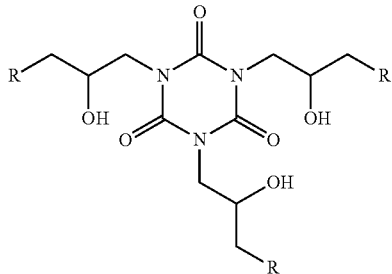

wherein each

R is a linear or branched aliphatic containing in the range of from 1 to 30 carbon atoms optionally substituted with hydroxy, ether, amide, silane, siloxane, ketone, urea and/or urethane groups.

2. The coating composition of claim 1 wherein R is of the formula $—(OR^2)_n—OR^3$; wherein $R^2$ is $—CH_2CH_2—$, $—CH_2CH(CH_3)—$, $—(CH_2)_4—$ or a combination thereof; and $R^3$ is H or an alkyl group containing from 1 to 6 carbon atoms and n is in the range of from 2 to 15.

3. The coating composition of claim 1 wherein R is a hydroxy functional alkyl containing in the range of from 1 to 27 carbon atoms.

4. The coating composition of claim 1 wherein R is $—OC(O)N(H)C_6H_{13}$.

5. The coating composition of claim 1 further comprising a crosslinking component wherein said crosslinking component is selected from the group consisting of polyisocyanates, melamines, blocked polyisocyanates and a combination thereof.

6. The coating composition of claim 1 wherein said coating composition is a primer composition, a basecoat composition or a clearcoat composition.

7. A method of producing a coating on a substrate; said method comprising the steps of; (i) applying a layer of a coating composition onto the surface of a substrate; and (ii) curing said layer of coating composition, wherein said coating composition comprises a hydroxy functional isocyanurate of the structure

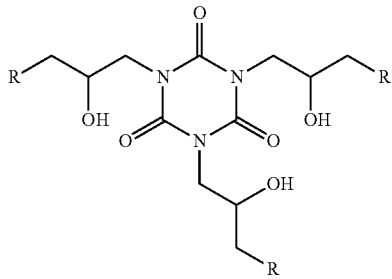

wherein each R is a linear or branched aliphatic containing in the range of from 1 to 30 carbon atoms optionally substituted with hydroxy, ether, amide, silane, siloxane, ketone, urea and/or urethane groups.

8. The method of claim 7 wherein R is of the formula $—(OR^2)_n—OR^3$; wherein $R^2$ is $—CH_2CH_2—$, $—CH_2CH(CH_3)—$, $—(CH_2)_3—$, $—(CH_2)_4—$ or a combination thereof; and $R^3$ is H or an alkyl group containing from 1 to 6 carbon atoms and n is in the range of from 2 to 15.

9. The method of claim 7 wherein R is a hydroxy functional alkyl containing in the range of from 1 to 27 carbon atoms.

10. The method of claim 7 wherein R is $—OC(O)N(H)C_6H_{13}$.

11. The method of claim 7 further comprising a crosslinking component wherein said crosslinking component is selected from the group consisting of polyisocyanates, melamines, blocked polyisocyanates and a combination thereof.

12. A hydroxy functional isocyanurate of the formula

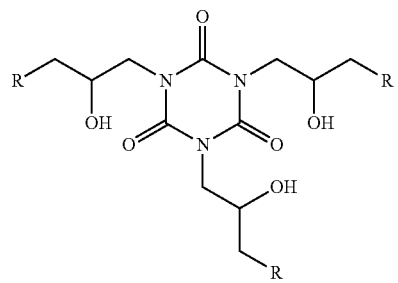

wherein each R is a linear or branched aliphatic containing in the range of from 1 to 30 carbon atoms optionally substituted with hydroxy, ether, amide, silane, siloxane, ketone, urea and/or urethane groups.

13. The hydroxy functional isocyanurate of claim 12 wherein R is of the formula $—(OR^2)_n—OR^3$; wherein $R^2$ is $—CH_2CH_2—$, $—CH_2CH(CH_3)—$, $—(CH_2)_3—$, $—(CH_2)_4—$ or a combination thereof; and $R^3$ is H or an alkyl group containing from 1 to 6 carbon atoms and n is in the range of from 2 to 15.

14. The hydroxy functional isocyanurate of claim 12 wherein R is a hydroxy functional alkyl containing in the range of from 1 to 27 carbon atoms.

15. The hydroxy functional isocyanurate of claim 12 wherein R is $—OC(O)N(H)C_6H_{13}$.

16. A method of producing the hydroxy functional isocyanurate of claim 12 said method comprising contacting cyanuric acid with an aliphatic epoxide, an epoxy functional ether, an epoxy functional ketone, an epoxy functional alcohol or an epoxy functional urethane.

* * * * *